United States Patent [19]

Butter et al.

[11] Patent Number: 4,593,147
[45] Date of Patent: Jun. 3, 1986

[54] SYNTHESIS OF NEOALKANES

[75] Inventors: Stephen A. Butter, Allentown; Ilse Stoll, Bethlehem, both of Pa.

[73] Assignee: Air Products and Chemicals, Inc., Allentown, Pa.

[21] Appl. No.: 667,173

[22] Filed: Nov. 1, 1984

[51] Int. Cl.$^4$ .................................................. C07C 1/00
[52] U.S. Cl. ...................................... 585/733; 585/700
[58] Field of Search ........................................... 585/733

[56] References Cited

U.S. PATENT DOCUMENTS

| 1,839,974 | 1/1932 | Lazier | 568/885 |
|---|---|---|---|
| 2,091,800 | 8/1937 | Adkins et al. | 568/885 |
| 2,110,483 | 3/1938 | Guyer et al. | 568/885 |
| 2,275,152 | 3/1942 | Lazier | 568/885 |
| 2,340,688 | 2/1944 | Richardson et al. | 568/884 |
| 2,389,598 | 11/1945 | Dawson | 585/733 |
| 2,422,670 | 6/1947 | Haensel et al. | 260/683.6 |
| 2,422,674 | 6/1947 | Haensel et al. | 260/683.6 |
| 2,422,675 | 6/1947 | Haensel et al. | 260/683.6 |
| 2,607,807 | 8/1952 | Ford et al. | 260/683.6 |
| 2,986,577 | 5/1961 | Kurhajec | 260/488 |
| 3,203,998 | 8/1965 | House et al. | 585/733 |
| 3,280,199 | 10/1966 | Schmerling | 568/884 |
| 3,338,949 | 8/1967 | Hagemeyer, Jr. et al. | 568/884 |
| 3,361,832 | 1/1968 | Pine et al. | 568/885 |
| 3,478,112 | 11/1969 | Adam et al. | 260/617 |
| 3,920,766 | 11/1975 | Jublin, Jr. et al. | 585/733 |
| 3,923,694 | 12/1975 | Cornthwaite | 252/463 |
| 3,961,037 | 6/1976 | Davies et al. | 423/656 |
| 3,985,814 | 10/1976 | Dougherty | 260/635 D |
| 4,104,478 | 8/1978 | Trivedi | 568/885 |
| 4,149,021 | 4/1979 | Wall | 568/864 |
| 4,249,031 | 2/1981 | Drent et al. | 585/733 |
| 4,279,781 | 7/1981 | Dienes et al. | 252/463 |
| 4,283,581 | 8/1981 | Wilkes | 568/864 |
| 4,398,039 | 8/1983 | Pesa et al. | 560/265 |
| 4,405,819 | 9/1983 | Duckwall, Jr. | 568/814 |
| 4,433,175 | 2/1984 | Kaufhold | 568/885 |
| 4,443,639 | 4/1984 | Pesa et al. | 568/885 |
| 4,465,889 | 8/1984 | Anthony et al. | 585/733 |

FOREIGN PATENT DOCUMENTS

| 702753 | 1/1965 | Canada | 260/629 |
|---|---|---|---|
| 1021354 | 11/1977 | Canada | 585/733 |
| 032237A | 2/1982 | Japan . | |
| 03854 | 11/1982 | PCT Int'l Appl. | 585/73 |
| 1543327 | 2/1942 | United Kingdom | 585/733 |
| 1734431 | 8/1955 | United Kingdom | 585/733 |
| 899113 | 1/1980 | U.S.S.R. . | |

OTHER PUBLICATIONS

Jones et al., *Ind. Eng. Chem.* (Anal. Ed.), vol. 17 (1949), p. 349.
Whitmore et al., *J. Am. Chem. Soc.*, vol. 55 (1933), p. 3803.
Whitmore et al., *J. Am. Chem. Soc.*, vol. 61 (1939), p. 1586.
Whitmore et al., *J. Am. Chem. Soc.*, vol. 63 (1941), p. 124.
Landa et al., *Chem. Listy*, vol. 51 (1957), 452–458.
Landa et al., *Chem. Listy*, vol. 50 (1956), 569–572.
Puzitskii et al., *Neftekhimiya*, vol. 7(2) (1967), 280–285.
Shutikova et al., *Tr. Vses. Nauch.-Issled. Inst. Natur. Dushist. Veschestv*, No. 7 (1965), 16–20.
Vedage et al., *J. Catalysis*, vol. 77 (1982), p. 558.
Adkins et al., *J. Am. Chem. Soc.*, vol. 72 (1950), 2626.
Klier, "Methanol Synthesis," in *Advances in Catalysis*, vol. 31, pp. 258–271.
Haensel et al., *J. Am. Chem. Soc.*, vol. 68 (1946), 345.

*Primary Examiner*—Andrew H. Metz
*Assistant Examiner*—Helane Myers
*Attorney, Agent, or Firm*—Richard A. Dannells, Jr.; James C. Simmons; E. Eugene Innis

[57] ABSTRACT

Neoalkanes of the formula $R_1R_2R_3CCH_3$ are synthesized by hydrogenation of a neoacid of the formula $R_1R_2R_3CCOOH$ or a neoalcohol of the formula $R_1R_2R_3CCH_2OH$, wherein $R_1$, $R_2$ and $R_3$ are the same or different alkyl of 1–10 carbon atoms, at a temperature of 250°–500° C. over a copper oxide/zinc oxide catalyst.

28 Claims, 2 Drawing Figures

FIG.1a  Neopentanol in Hexane Feed
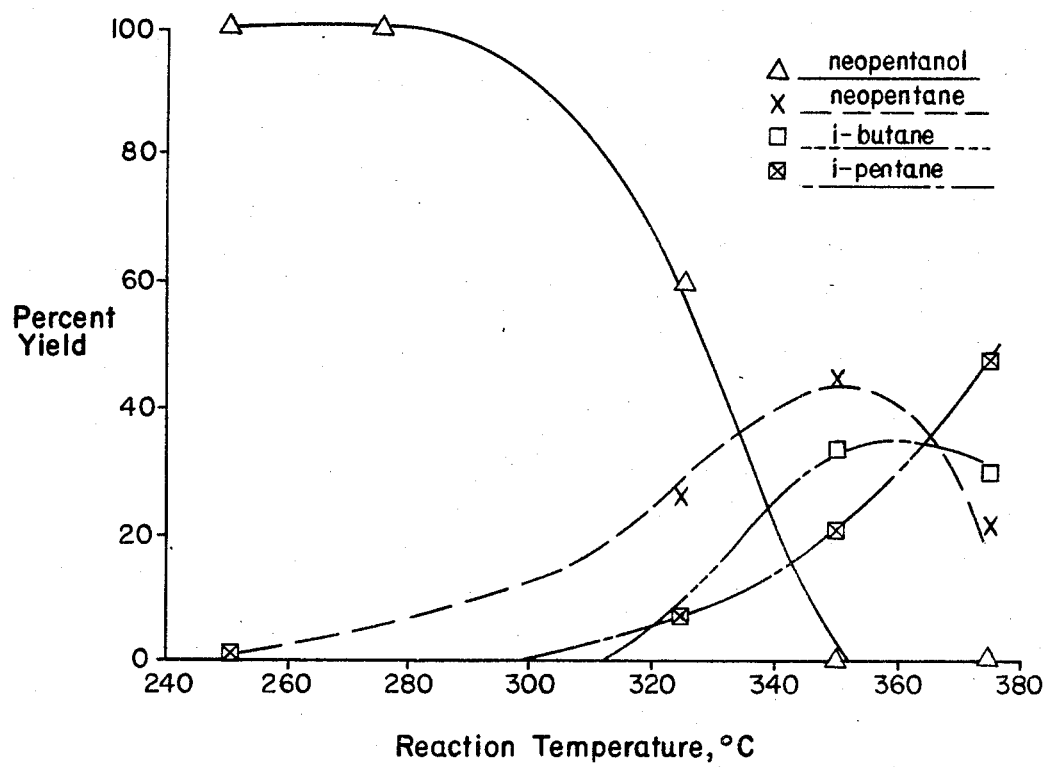
FIG.1b  Pivalic Acid in Hexane Feed
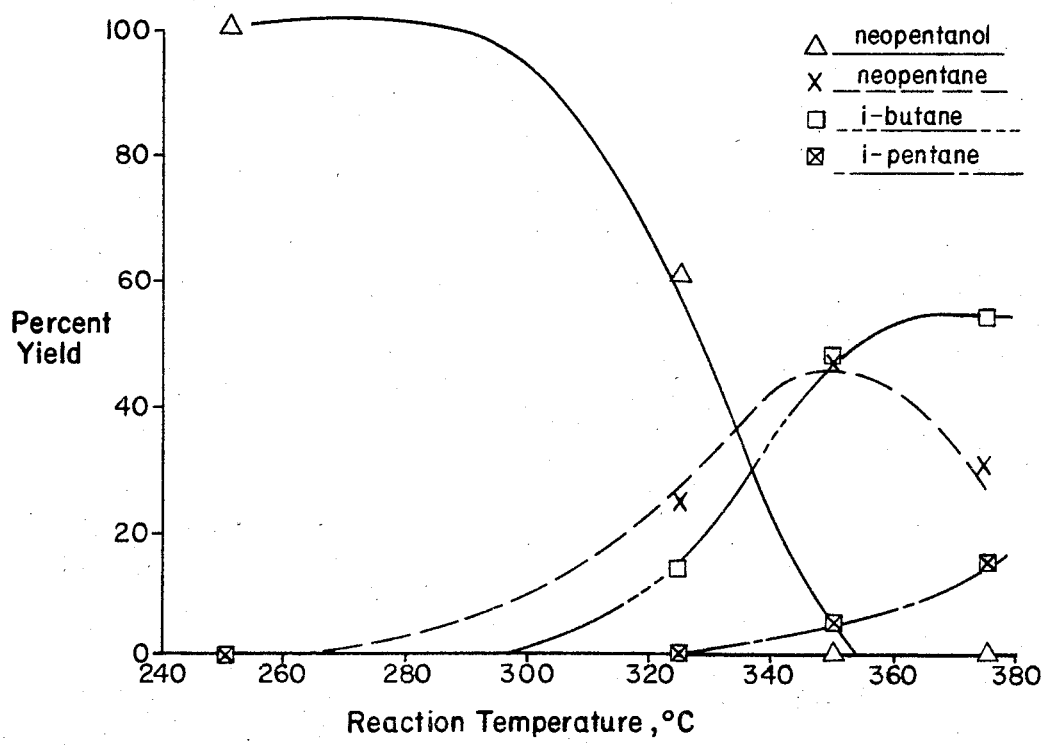

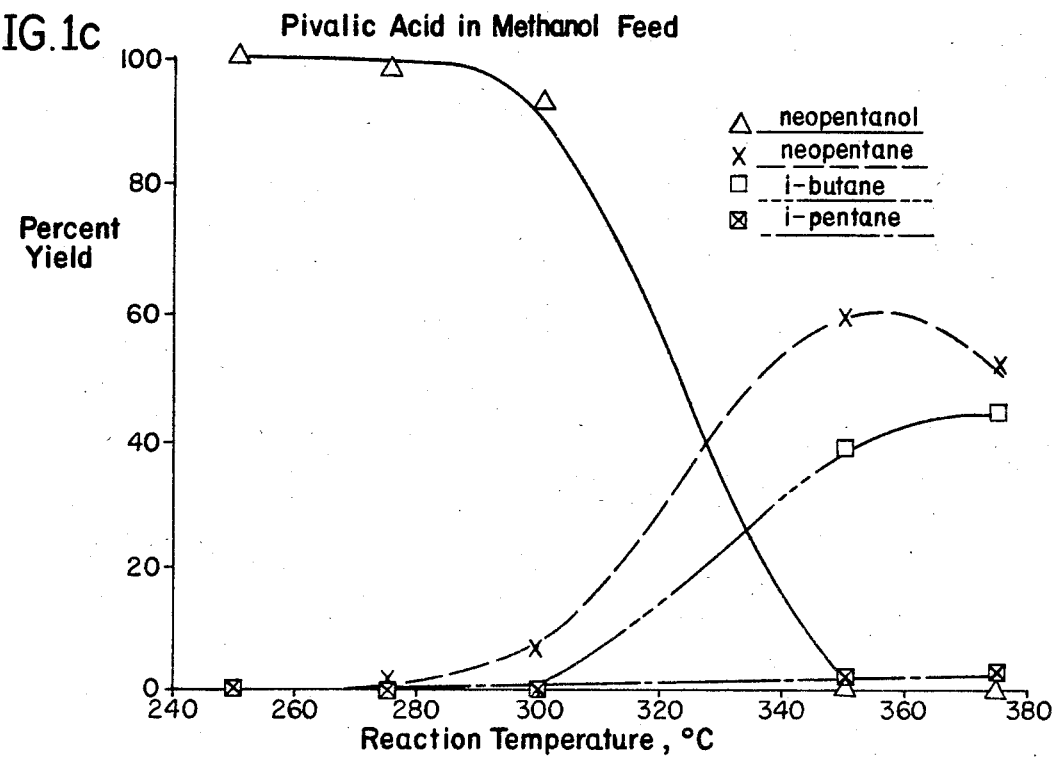
FIG.1c Pivalic Acid in Methanol Feed
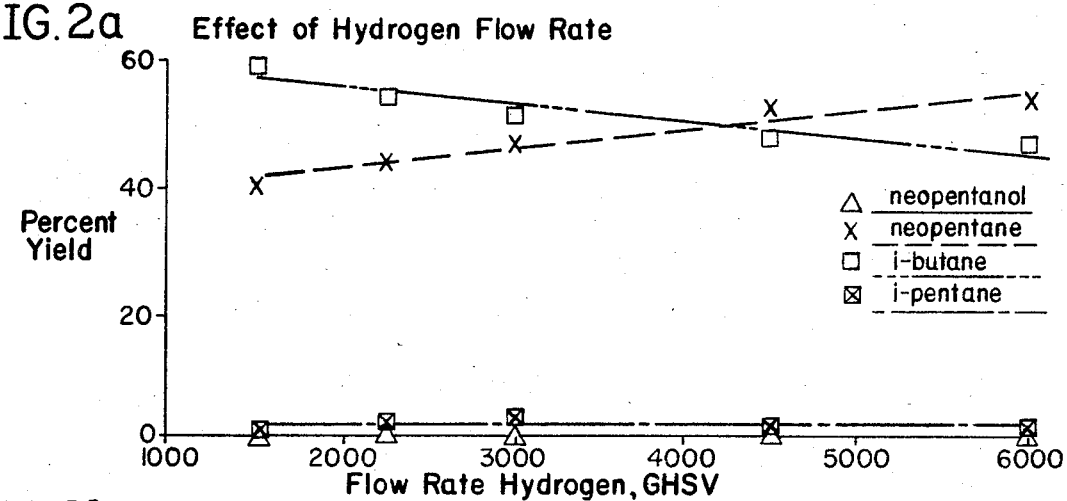
FIG.2a Effect of Hydrogen Flow Rate
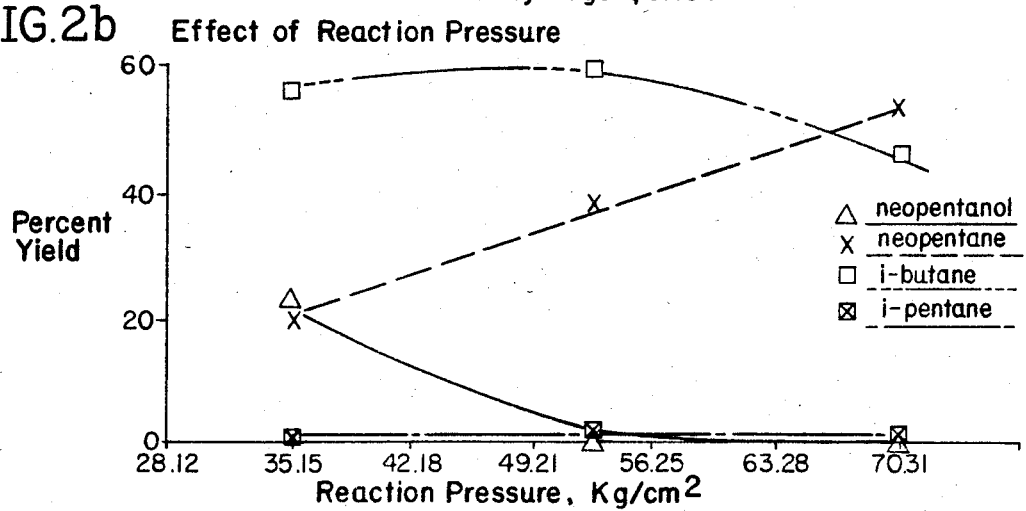
FIG.2b Effect of Reaction Pressure

SYNTHESIS OF NEOALKANES

TECHNICAL FIELD

This invention relates to processes for the synthesis of neoalkanes from corresponding neoacids or neoalcohols.

Neoalkanes are compounds of the formula $R_1R_2R_3CCH_3$. Typically, each R is alkyl of 1-10 carbon atoms. The lowest member of this series of compounds, in which each R is methyl, is neopentane, $(CH_3)_4C$. Neopentane is of commercial interest because it is condensible gas (b.p. $+9°$ C.), which can be used as a heat exchange fluid in solar panels. Neopentane occurs in concentrations below about 0.1% in refinery streams, so that its isolation from these sources usually is not economical. The isolation and identification of neopentane in refinery butanes has been described by Jones et al., *Ind. Eng. Chem.* (Anal. Ed.), vol. 17 (1949), at page 349.

Neoacids and neoalcohols, however, should provide economically competitive starting materials for synthesis of relatively pure neoalkanes, such as neopentane, by catalytic hydrogenation.

BACKGROUND ART

The preparation of alkyl-substituted 1,1,1-trialkylethanes, such as neopentane, by hydrogenation of a corresponding tertiary alkylcarbinol has been proposed by Ford et al. (U.S. Pat. No. 2,440,678). A cobalt hydrogenation catalyst was used, at temperatures of 100°-400° C. and pressures above 7 Kg/cm$^2$. However, a preference was recited for pressures above 70 Kg/cm$^2$ and temperatures of 175°-375° C.

Prior routes to neopentane include synthesis for a tert-butyl halide and dimethyl zinc, as recited by Whitmore et al., *J. Am. Chem. Soc.*, vol 55 (1933), page 3803:

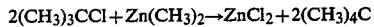
$$2(CH_3)_3CCl + Zn(CH_3)_2 \rightarrow ZnCl_2 + 2(CH_3)_4C$$

An alternative route to neopentane, in accordance with Whitmore et al., *J. Am. Chem. Soc.*, vol. 61 (1939), page 1586, is by reaction between neopentyl iodide and potassium hydroxide:

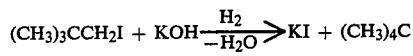
$$(CH_3)_3CCH_2I + KOH \xrightarrow[-H_2O]{H_2} KI + (CH_3)_4C$$

It was further shown by Whitmore et al., *J. Am. Chem. Soc.*, vol 63 (1941), page 124, that reaction between neopentyl chloride and sodium produced neopentane, as well as 1,1-dimethylcyclopropane:

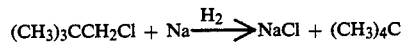
$$(CH_3)_3CCH_2Cl + Na \xrightarrow{H_2} NaCl + (CH_3)_4C$$

Duckwall, Jr., in U.S. Pat. No. 4,405,819, has proposed obtaining alcohols from acids, which can be branched, using a metal-containing hydrogenation catalyst. However, the process requires a sweep gas, containing carbon monoxide, and does not appear to contemplate the further reduction of alcohol to alkane.

Wall has recited, in U.S. Pat. No. 4,149,021, the hydrogenation of esters, apparently of linear acids, using a cobalt/zinc/copper catalyst. The use of a copper/zinc oxide catalyst is said to be undesirable, because of catalyst instability.

Wilkes has disclosed, in U.S. Pat. No. 4,283,581, a process for hydrogenating feed stocks, such as glycolide and glycolates, to ethylene glycol, using a copper/zinc oxide catalyst, supported on silica. The reference indicates that, using a similar copper/zinc oxide/alumina catalyst, low conversions are obtained at about 190° C. and a pressure of 105 Kg/cm$^2$. Higher conversion (46%) was reported at a higher temperature.

The reduction of branched esters, e.g., pivalic acid esters, to alcohols, has been disclosed by Kurhajec in U.S. Pat. No. 2,986,577. A copper chromite catalyst was employed. The reaction required a high hydrogen pressure, of the order of 232 Kg/cm$^2$.

Pine et al. (U.S. Pat. No. 3,361,832) have accomplished conversion of branched acids, generally in the form of esters, to alcohols employing a molybdenum sulfide catalyst, under relatively low temperatures and pressures. However, for high selectivity toward corresponding alcohols, e.g., neoheptanol, the use of high pressures, well above about 70 Kg/cm$^2$, are required.

Neopentane is reported as being a minor product (0.4%) of the hydrogenation of methyl pivalate, using a molybdenum sulfide catalyst, Landa et al., *Chem. Listy*, vol. 51 (1957), 452-458. The major product (74.0%) was 2-methylbutane. Under the same conditions, 71% of neopentanol was converted to 24% of neopentane and 30% of isopentane.

Landa et al. have also reported hydrogenation of less highly branched alcohols to hydrocarbons, *Chem. Listy*, vol. 50 (1956), 569-572.

Reduction of alpha,alpha-dimethylalkanoic acids over copper chromite catalyst has been recited by Puzitskii et al., *Neftekhimiya*, vol. 7 (2) (1967), 280-285. Reduction of methyl pivalate to neopentyl alcohol over copper chromite has been reported by Shutikova et al., *Tr. Vses. Nauch.-Issled. Inst. Natur. Dushist. Veshchestv*, no. 7 (1965), 16-20.

The use of Adkins' copper-chromium oxide catalyst, *J. Am. Chem. Soc.*, vol. 72 (1950), 2626-2629, was recited as a route to neopentanol from methyl pivalate, Landa et al., *Chem. Listy*, vol. 51 (1957), 452-458.

Catalytic reduction of acids, having branched structures, other than of the alpha, alpha, alpha-trisubstituted type, are disclosed by:
U.S. Pat. No. 2,607,807: Ford et al.
U.S. Pat. No. 3,478,112: Adam et al.
U.S. Pat. No. 3,920,766: Jubin, Jr. et al.
U.S. Pat. No. 4,433,175: Kaufhold Hydrogenation of linear acids or their esters to corresponding alcohols has been disclosed in:
U.S. Pat. No. 1,839,974: Lazier
U.S. Pat. No. 2,091,800: Adkins et al.
U.S. Pat. No. 2,110,483: Guyer et al.
U.S. Pat. No. 2,275,152: Lazier
U.S. Pat. No. 2,340,688: Richardson et al.
U.S. Pat. No. 3,985,814: Dougherty
U.S. Pat. No. 4,104,478: Trivedi
U.S. Pat. No. 4,398,039: Pesa et al.
U.S. Pat. No. 4,443,639: Pesa et al.
Japan Pat. No. 57032237-A: Sumitomo Chemical K.K.
German OLS No. 2,613,226: Demmering (Sept. 9, 1977)
WO 82/03854: Davy McKee
Soviet Union Pat. No. 899113: Sultanov et al.
Vedage et al., *J. Catalysis*, vol. 77 (1982), page 558.

Of the foregoing, the Vedage et al. article discloses employing a copper/zinc oxide catalyst, normally used for methanol synthesis, to hydrogenate propanoic acid to propanol. The Davy McKee patent is of similar interest with respect to reduction of butyl butyrate or other esters. The reference contemplates reduction of branched esters, e.g. isobutyrates.

Demethylation of hydrocarbons, under hydrogenation conditions, has been disclosed by Haensel et al., U.S. Pat. Nos. 2,422,670; 2,422,674 and 2,422,675 and *J. Am. Chem. Soc.*, vol. 68 (1946), page 345.

It is accordingly apparent that direct synthesis of highly branched hydrocarbons, particularly of the neoalkane type, from either neoacids or neoalcohols, is a synthetic route which has not heretofore been utilized successfully.

DISCLOSURE OF INVENTION

In one aspect, this invention relates to a process for the synthesis of 1,1,1-trialkylalkanes of the formula $R_1R_2R_3CCH_3$ by hydrogenation of a neoacid of the formula $R_1R_2R_3CCOOH$, wherein $R_1$, $R_2$ and $R_3$ each are alkyl of 1-10 carbon atoms, at 250°-500° C. over a copper oxide/zinc oxide catalyst.

In another aspect, this invention relates to the synthesis of a neoalkalkane from a corresponding neoalcohol of the formula $R_1R_2R_3CCH_2OH$, wherein $R_1$, $R_2$ and $R_3$ are as above, at 250°-500° C. over a copper oxide/zinc oxide catalyst.

Catalytic hydrogenation of representative substrates for the practice of this invention may be expressed, in the case of pivalic acid and neopentanol by the following equations:

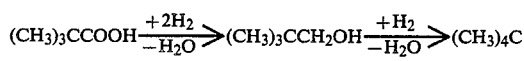

Neoacids are available commercially from the hydrocarboxylation of branched olefins (Koch reaction), as represented by the equation:

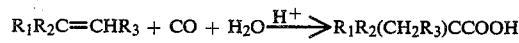

It is shown in this specification that representative neoacids, such as pivalic and neodecanoic acids, can be used as substrates for the practice of this invention. Similarly, neoalcohols can be used as sources of neoalkanes.

Other types of neo-compounds, which can be used as alternative substrates, include corresponding neoglycols or neodiacids, or their esters. Exemplary materials include dimethylmalonic acid and neopentyl glycol. Branched chain alcohols, used as feeds for the process of this invention, can be obtained as described by Kurhajec, Canadian Pat. No. 702,753; Schmerling, U.S. Pat. No. 3,280,199 and Hagemeyer, Jr. et al., U.S. Pat. No. 3,338,949.

It is preferred that the feed utilized in the practice of this invention is a neoacid or neoalcohol, wherein $R_1$ and $R_2$ each are methyl. Most preferably, all three alkyls are methyl. Accordingly, most preferred feeds for the practice of this invention are pivalic acid and neopentanol. Pivalic acid is also known as neopentanoic acid, 2,2,2-trimethylacetic acid or 2,2-dimethylpropanoic acid. Other names for neopentanol are 2,2-dimethylpropanol, 2,2,2-trimethylethanol or neopentyl alcohol.

A further preferred feed is known as neodecanoic acid, wherein $R_1$ and $R_2$ are methyl and $R_3$ is an alkyl of six carbon atoms.

Products obtained by the process of this invention, whether starting from a neoacid or a neoalcohol, or by reducing a neoacid stepwise through a neoalcohol intermediate include, in the case of pivalic acid, neopentane, isobutane and isopentane. Neopentane is also known as 2,2-dimethylpropane, 1,1,1-trimethylethane or tetramethylmethane. Isobutane is also known as 2-methylpropane and isopentane as 2-methylbutane. The isoparaffins, isolated as by-products from the process of this invention, are thought to originate by demethylation or isomerization of the feed or intermediates.

Operative conditions for the process of this invention, whether starting from a neoacid or a neoalcohol, are temperatures of 250°-500° C., hydrogen pressure of 3.5-700 Kg/cm², substrate feed rate of 0.1 mM-1000 mM/g catalyst/h, and hydrogen feed rate of 75-8000 ml/g catalyst/h.

In synthesizing neopentane from neopentanol, it is preferred to use a temperature of 325°-375° C. and a hydrogen feed rate of 1500-6000 ml/g catalyst/h. Under these temperature conditions, a neoalcohol feed rate of 0.2-4.9 mM/g catalyst/h is preferred. Also, in this temperature range, it is preferred to use hydrogen pressures of 35-140 Kg/cm².

Most preferably, for the synthesis of neopentane from neopentanol, the temperature is 335°-365° C., the hydrogen feed rate is 4000-6000 ml/g catalyst/h, the neopentanol flow rate is 0.2-2.2 mM/g catalyst/h and the hydrogen pressure is 56-70 Kg/cm².

If a source of neoalcohol is not readily available, it is possible to reduce a neoacid to a corresponding neoalcohol as a preliminary step. This is done over the same type of copper oxide/zinc oxide catalyst at 200°-325° C. It is preferred that this reduction be carried out at 225°-300° C. under a hydrogen pressure of 35-70 Kg/cm², for the case of neopentane synthesis.

For the direct synthesis of neoalkanes from neoacids, using a copper oxide/zinc oxide catalyst, the hydrogenation is carried out under the same conditions as for reduction of the corresponding neoalcohols. In this process, it is preferred that alkyl is linear and each of $R_1$ and $R_2$ are methyl. In a most preferred case, all of $R_1$, $R_2$ and $R_3$ are methyl and the hydrogenation is carried out at 335°-365° C.

In the direct synthesis of neoalkanes from neoacids, it is preferred to use a hydrogen pressure of 35-140 Kg/cm² and hydrogen flow rate of 1500-6000 ml/g catalyst/h. A neoacid feed rate of 0.2-4.9 mM/g catalyst/h is preferred.

In carrying out neoalkane synthesis according to this invention, difficulties can occur in handling neoacids or neoalcohols, which may be solids under the conditions used. In some cases, the feed can be diluted with a solvent, which is inert to the reaction condition and which has a boiling point, such that it can be readily removed from the product stream by distillation. Hydrocarbons and alcohols are representative of diluents which can be used. If a diluent is used, the preferred amount is 5-50% by weight of feed. Preferred diluents are hexane and methanol.

Alternatively, low melting neoacids or neoalcohols can be melted and fed to the reactor in liquid form. Accordingly, use of undiluted feed is feasible and preferred.

Products, obtained by the process of this invention, can be purified by distillation or other well known techniques. The products may contain isoalkanes having the same or one fewer carbon than the feed material, thought to arise by rearrangement and demethylation. It is preferred to remove isoalkanes by adsorption on a medium pore zeolite or molecular sieve. The neoalkane product is not adsorbed on such a sieve, for example, ZSM-5, 11, 12, 23, 35, 38 or 48.

Catalysts, used in the process of this invention, are supported copper oxide/zinc oxide catalysts, of the type used in the synthesis of methanol by reaction between carbon monoxide and hydrogen. The binary copper/zinc oxide system is as described by Klier, "Methanol Synthesis," in *Advances in Catalysis*, vol. 31, Eley et al., editors, Academic Press, New York (1982), particularly at pages 258-271. These catalysts can be prepared on a variety of supports, such as, oxides of aluminum, silicon, zirconium, titanium, calcium, chromium or magnesium. The catalysts consist of coprecipitated CuO/ZnO, for example, from copper and zinc nitrate solutions. The compositional range employed is 12-66% as copper (II) oxide, 17-62% as zinc oxide and 4-38% carrier, e.g. alumina.

In high zinc catalysts, hydroxycarbonates are predominant, whereas in high copper catalysts, the main catalyst component is copper hydroxy nitrate, $Cu_2(OH)_3NO_3$. Calcination of either type of material in air at about 350° C. gave a mixture of Cu(II) oxide in the tenorite form and wurtzite zinc oxide. Reduction of these materials converted the copper (II) oxide to elemental copper, whereas the ZnO was unreduced. Accordingly, the catalyst are thought to be intimate mixtures of small particles of copper and zinc oxide.

A methanol synthesis catalyst, comprising copper and zinc oxide, supported on aluminum oxide, has been described by Stiles in Canadian Pat. No. 1,021,354. This catalyst is thought to consist of copper oxide-zinc oxide having Cu:Zn ratios of 1:1 to 8:1, preferably about 4:1. The catalyst is relatively free of sodium or sulfur.

Other catalysts, appropriate for methanol synthesis and for the reactions of this invention are disclosed by Cornthwaite, U.S. Pat. No. 3,923,694; Davies et al., U.S. Pat. No. 3,961,037 and Dienes et al., U.S. Pat. No. 4,279,781, herein incorporated by reference. In addition, catalysts described by Vedage and Davy McKee, supra, can be used.

It will be understood that, in the specification and claims, "copper oxide/zinc oxide" includes corresponding reduced forms, whether formed during activation or during the reactions of this invention.

Preferred catalysts for the utilization of this invention are those supported on alumina, more preferably comprising 80-95% by weight of copper oxide/zinc oxide in 8:1-1: weight ratio and 20-5% by weight of alumina. Most preferred are catalysts, wherein the weight ratio of copper oxide/zinc oxide is 4:1 to 1:1.

The catalyst, used in the process of this invention, is preferably activated by heating with 1-10% by volume of hydrogen in nitrogen at 250°-375° C. for 2-30 h.

BRIEF DESCRIPTION OF THE DRAWINGS

In FIG. 1 is shown the relationship between reaction temperature and products obtained by hydrogenation of neopentanol or pivalic acid.

In FIG. 2 is shown the effects of hydrogen flow rate and reaction pressure on yields of neopentane from pivalic acid.

BEST MODE FOR CARRYING OUT THE INVENTION

In a most preferred process for synthesizing neopentane from neopentanol, the reaction is carried out at 335°-365° C., the hydrogen feed rate is 4000-6000 ml/g catalyst/h, the neopentanol flow rate is 0.2-2.2 mM/g catalyst/h and the hydrogen pressure is 56-70 Kg/cm$^2$.

In a most preferred process for this synthesis of neopentane from pivalic acid, the reaction temperature is 335°-365° C., the hydrogen pressure is 56-70 Kg/cm$^2$, the hydrogen flow rate is 4000-6000 ml/g catalyst/h and the pivalic acid feed rate is 0.2-2.2 mM/g catalyst/h. The pivalic acid is preferably diluted with 5-50% by weight of hexane or methanol.

Most preferred catalysts are as recited above.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Experiments were done in a fixed-bed catalyst screening reactor, comprising a vertical tubular cylindrical 316 stainless steel tube (3.175 cm outer diameter, 0.30 cm wall thickness), inside of which was mounted a cylindrical quartz reactor (1.905 cm diameter), containing a catalyst bed 20 mm thick, packed above and below the catalyst bed with quartz wool. Gas was fed into the system from cylinders, pressure being controlled by back pressure regulators, in upflow fashion. Liquid was fed through a 0.16 cm stainless steel feedline downwardly into the quartz reactor. Liquid flow was controlled by a high pressure liquid pump. The temperature within the system was measured by a thermocouple located at the center of the catalyst bed. Product, removed from the system through a stainless steel tube at the bottom of the reactor system, was fed directly into an on-line gas chromatographic analyzer through a line heat traced at 175° C.

Hydrogenation catalyst (CuO/ZnO/alumina) pellets were ground in a porcelain mortar. A charge of 4.00 g of sieved catalyst (10-16 Taylor mesh fraction) was loaded into the quartz reactor and was reduced at a pressure of 5.6 Kg/cm$^2$ and 600 GHSV (STP) as follows:

1. under a stream of nitrogen, the temperature was increased from 30° C. to 250° C. at a rate of 0.5°-5°/min
2. under a stream of hydrogen (2% by volume) in nitrogen, the temperature was held at 250° C. for 0-16 h;
3. under a stream of hydrogen (2% by volume) in nitrogen, the temperature was increased from 250° to 350°-375° C. at a rate of 0.15°-1.5°/min and
4. catalyst was held at 350°-375° C. for 2-30 h in a stream of hydrogen (2% by volume) in nitrogen.

Product leaving the system was analyzed by gas chromatography, using a Perkin Elmer Sigma 2000, with a 0.32×15.24 cm. SS column packed with poropak Q. The carrier gas was helium and the flow rate was 30 ml/min. Flame ionization and hot wire detectors were employed. The injector was a Valco gas valve with a 1.0 ml gas loop at 200° C. The program used provided for a temperature increase of 15° C./min from 200°–250° C., after which the temperature was held at 250° C. for 10 min. A Perkin Elmer Data Station 3600 integrator was used to measure peak areas, generated by a flame ionization detector. An external standard of 0.5% neopentane by volume in nitrogen was used for determination of flame ionization detector response area to areas obtained from the product stream.

Material balance calculations compared the sum of mM of products to mM of substrate in the feed. Response factors and yields were calculated by the equations:

$$RF_{std} = \frac{FID_{std} \times 0.1}{[std]/(100 \times 22.4) \times MW_{std} \times (\text{ml gas loop})}$$

and

% product yield =

$$\frac{0.1}{RF_{std}} \times \frac{\text{ml reactor exit flow/h} \times 100}{\text{mM substrate/h} \times MW_{prod}} \times \frac{FID_{prod}}{\text{ml gas loop}}$$

wherein RF is the absolute response factor for 0.1 mg of standard compound in 1.0 ml of standard gas mixture at analysis conditions, using a flame ionization detector, [std] is the molar concentration of standard compound in the standard gas mix, MW is molecular weight and FID is measured flame ionization detector response in absolute area counts.

Other definitions, used in the Examples below, include:

catalyst selectivity for neopentane:

$$\frac{\text{mM neopentane in product}}{\text{mM of products}}$$

percent substrate conversion:

$$\frac{\text{mM products}}{\text{mM substrate in feed}} \times 100$$

percent neopentane yield:

$$\frac{\text{mM neopentane in product}}{\text{mM substrate in feed}} \times 100$$

gas hourly space velocity (GHSV):

$$\frac{\text{ml feed gas}}{\text{min}} \times \frac{60}{\text{g catalyst}}$$

Steady state conditions, unless otherwise indicated, were reached after two hours on line.

In the Examples, catalysts are defined by alumina content, the balance being CuO/ZnO in the stated weight ratio, before activation or reduction.

EXAMPLE 1

Pivalic acid in hexane (80.6% by weight of pivalic acid) was fed to a reactor charged with 4.00 g of 2:1 CuO/ZnO/10% alumina catalyst. The feed rate with respect to pivalic acid was 6.5 mM/h, the hydrogen flow rate 300 ml/min at STP, the pressure 70.3 Kg/cm$^2$ and the temperature 350° C. Under steady state conditions, the product contained 46 mol % of neopentane, 49 mol % of isobutane and 5 mole % of isopentane. No unconverted pivalic and no neopentanol were detected.

EXAMPLE 2

Under conditions, otherwise as in Example 1, but using neopentanol in hexane feed (50% by weight of neopentanol) at a feed rate of 8.7 mM/h with respect to neopentanol, the product under steady state conditions contained 45 mol % of neopentane, 33 mol % of isobutane and 22 mol % of isopentane. All of the neopentanol was converted to products.

These examples show that both neopentanol and pivalic acid produce the same amount of neopentane. These experiments further suggest that, using pivalic acid feed, demethylation to isobutane is the predominant side reaction whereas, with neopenantol feed, isomerization to isopentane is the predominant side reaction.

EXAMPLE 3

Under conditions of Example 1, pivalic acid in methanol (85.7% by weight pivalic acid; 6.5 mM/h feed rate with respect to pivalic acid) produced 51 mol% of neopentane, 47 mol% of isobutane and 2 mol % of isopentane. Neither pivalic acid nor neopentanol was detected in the product stream.

Comparison of results of Examples 1 and 3 suggests that the use of a solvent does not significantly affect the product distribution. In addition, it appears that methyl pivalate, which would not be formed under conditions of Example 1, is not necessarily an intermediate in the process.

EXAMPLE 4

Under conditions, otherwise as in Example 1, but using a hydrogen flow rate of 100 ml/min, the product under steady state conditions contained 40 mol % of neopantane, 59 mol % of isobutane and 1 mol % of isopentane. Neither pivalic acid nor neopentanol was detected in the products.

EXAMPLE 5

Under conditions of Example 1, at a hydrogen flow rate of 400 ml/min, the product mixture at steady state operation contained 53 mol % of neopentane, 46 mol % of isobutane and 1 mol % of isopentane. Neither pivalic acid nor neopentanol was detected in the product.

Results of Examples 1, 4 and 5 suggest that lower hydrogen flow rates decrease neopentane formation, but increase formation of isobutane. Higher hydrogen flow rates cause higher yields of neopentane and lower yields of isobutane. It is therefore proposed that higher hydrogen flow rates prevent demethylation.

EXAMPLE 6

Under conditions, otherwise as in Example 1, but under a pressure of 35.2 Kg/cm$^2$, the product mixture at steady state operation contained 20 mol % of neopentane, 56 mol % of isobutane, 1 mol % of isopentane and 23 mol % of neopentanol. No unconverted pivalic acid was detected.

EXAMPLE 7

Pivalic acid in hexane (80.6% by weight of pivalic acid) is fed to a reactor charged with 2:1 CuO/ZnO/10% alumina catalyst at a feed rate of 6.5 mM/h, pressure of 140.6 Kg/cm$^2$ and temperature of 350° C. Under steady state conditions, a product mix, similar to that of Example 1, is obtained.

The results of Examples 1, 6 and 7 suggest that at lower reaction pressures, neopentane formation is decreased, but isobutane and neopentanol formation are increased. These experiments suggest that preferred pressure conditions for formation of neopentane are 35–140 Kg/cm$^2$.

EXAMPLE 8

Under conditions, otherwise as in Example 1, at a feed rate for pivalic acid of 1.6 mM/h, the product at steady state operation contained 70 mol % of neopentane, 26 mol % of isobutane and 4 mol % of isopentane. Neither unconverted pivalic acid nor neopentanol was detected.

EXAMPLE 9

Under conditions, otherwise as in Example 1, at a pivalic acid feed rate of 19.6 mM/h, the product under steady state operation contained 17 mol % of neopentane, 21 mol % of isobutane, 1 mol % of isopentane and 61 mol % of neopentanol. No unconverted pivalic acid was detected.

Examples 1, 8 and 9 suggest that increasing pivalic acid feed rate decreases formation of neopentane and increases formation of neopentanol. It appears that optimum feed rates for neopentane formation under the conditions recited range from 0.4 mM/g catalyst/h to 1.6 mM/g catalyst/h.

EXAMPLE 10

Under conditions, otherwise as in Example 1, employing a reaction temperature of 300° C. and hydrogen flow rate of 400 ml/min at STP, the product under steady state operation contained 7 mol % of neopentane and 93 mol % of neopentanol. None of unconverted pivalic acid, isobutane or isopentane was detected in the product.

EXAMPLE 11

Under conditions, otherwise as in Example 1, but using a reaction temperature of 325° C., the product under steady state operation contained 25 mol % of neopentane, 14 mol % of isobutane and 61 mol % of neopentanol. There was no isopentane or unconverted pivalic acid.

EXAMPLE 12

Using reaction conditions, otherwise as in Example 1, at a temperature of 375° C., the product under steady state operation contained 31 mol % of neopentane, 54 mol % of isobutane and 15 mol % of isopentane. Neither unconverted pivalic acid nor neopentanol was detected in the product stream.

Comparison of results of Examples 1, 10, 11 and 12 show that increasing reaction temperature increases neopentane yield and decreases neopentanol yield. The optimum temperature for neopentane formation appears to be about 350° C. At higher temperatures, neopentane formation decreases and isobutane and isopentane formation increase. Accordingly, preferred temperatures for overall conversion to neopentane are 325°–375° C., most preferably 335°–365° C.

EXAMPLE 13

Experiments were done, as in the foregoing Examples, to determine the effect of reaction temperature on product distribution from neopentanol or pivalic acid feeds. The 2:1 CuO/ZnO/10% alumina catalyst was used. The rate of substrate feed was varied from b 1.6–2.2 mM/g catalyst/h, the hydrogen flow rate was 4500–6000 GHSV (ml/g catalyst/h) and the pressure 70.3 Kg/cm$^2$. Catalyst from the experiments with the neopentanol/hexane mixture was used for the experiments with the pivalic acid/hexane mixture. Results at steady state operation are shown in Table 1 and in FIG. 1.

As shown in FIG. 1, neopentanol was essentially unconverted to hydrocarbon at 250° C., whereas pivalic acid was quantitatively converted to neopentanol.

At a reaction temperature of 325° C., 40 mol % of neopentanol was converted to hydrocarbons (26 mol % of neopentane, 7 mol % of isobutane, 7 mol % of isopentane and 60 mol % of unconverted neopentanol). At the same temperature, pivalic acid was converted to hydrocarbons (25 mol % of neopentane and 14 mol % of isobutane). The product also contained 61 mol % of neopentanol.

At a reaction temperature of 350° C., pivalic acid was converted completely to hydrocarbons: 59 mol % of neopentane, 39 mol % of isobutane and 2 mol % of isopentane from the pivalic acid/methanol feed under one set of conditions and 47 mol % of neopentane, 48 mol % of isobutane and 5 mol % of isopentane from the pivalic acid/hexane feed under another set of conditions.

Under the same conditions neopentanol was quantitatively converted to the hydrocarbons, neopentane (45 mol %), isobutane (34 mol %) and isopentane (21 mol %).

For the reactions done at 375° C., pivalic acid was converted to 52 mol % of neopentane, 45 mol % of isobutane and 3 mol % of isopentane (pivalic acid/methanol feed). The pivalic acid/hexane feed was also converted quantitatively: the products were 31 mol % of neopentane, 54 mol % of isobutane and 15 mol % of isopentane. Neopentanol was completely converted to other products, namely, 22 mol % of neopentane, 30 mol % of isobutane and 48 mol % of isopentane.

The results of these experiments show that the neopentane synthesis is preferably done at 325°–375° C. at the feed rates examined.

EXAMPLE 14

The effect of hydrogen flow rate on product distribution from feed consisting of pivalic acid/methanol (85.7:14.3 by weight) at 350° C., at a pressure

TABLE 1

| Feed | GHSV Hydrogen | Feed Rate mM/g cat/hr | Temp °C. | % Yield | | | |
|---|---|---|---|---|---|---|---|
| | | | | NeoC$_5$OH | NeoC$_5$ | i-C$_4$ | i-C$_5$ |
| Pivalic | 6000 | 1.6 | 250 | 100 | 0 | 0 | 0 |
| acid/methanol | | | 275 | 98 | 2 | 0 | 0 |
| (50:50 wt.) | | | 300 | 93 | 7 | 0 | 0 |
| | | | 350 | 0 | 59 | 39 | 2 |
| | | | 375 | 0 | 52 | 45 | 3 |
| Neopentanol/ | 4500 | 2.2 | 250 | 98 | 1 | 1 | 0 |
| hexane | | | 325 | 60 | 26 | 7 | 7 |

TABLE 1-continued

| Feed | GHSV Hydrogen | Feed Rate mM/g cat/hr | Temp °C. | % Yield NeoC$_5$OH | NeoC$_5$ | i-C$_4$ | i-C$_5$ |
|---|---|---|---|---|---|---|---|
| (66.7:33.3 wt.) | | | 350 | 0 | 45 | 34 | 21 |
| | | | 375 | 0 | 22 | 30 | 48 |
| Pivalic acid/hexane (80.6:19.4 wt.) | 4500 | 1.6 | 250 | 100 | 0 | 0 | 0 |
| | | | 325 | 61 | 25 | 14 | 0 |
| | | | 350 | 0 | 47 | 48 | 5 |
| | | | 375 | 0 | 31 | 54 | 15 | of 70.3 Kg/cm$^2$, 1500–6000 GHSV of hydrogen and pivalic acid feed rate of 1.6 mM/g catalyst/h, was investigated. The catalyst was 2:1 CuO/ZnO/10% alumina. The effect of hydrogen pressure on product distribution was also determined under the same conditions, using a hydrogen flow rate of 4500 GHSV and a pressure range of 35.2–70.3 Kg/cm$^2$. Results are shown in Table 2 and FIG. 2.

These results suggest that selectivity toward neopentane is increased and selectivity toward isobutane is decreased with increasing hydrogen flow rate, up to a maximum of about 4500 GHSV. At higher flow rates, selectivity was not significantly affected. Selectivity toward isopentane did not appear to be influenced by hydrogen flow rate.

TABLE 2
Effect of Hydrogen Flow Rate and Reaction Pressure on Product Distribution

| Kg/cm$^2$ Pressure | GHSV Hydrogen | % Yield Neopentanol | Neopentane | i-Butane | i-Pentane |
|---|---|---|---|---|---|
| 70.3 | 1500 | 0 | 40 | 59 | 1 |
| 70.3 | 2250 | 0 | 44 | 54 | 2 |
| 70.3 | 3000 | 0 | 47 | 51 | 2 |
| 70.3 | 4500 | 0 | 52 | 47 | 1 |
| 70.3 | 6000 | 0 | 53 | 46 | 1 |
| 35.2 | 4500 | 23 | 20 | 56 | 1 |
| 52.7 | 4500 | 0 | 38 | 60 | 2 |

TABLE 3
Effect of Pivalic Acid Feed Rate on Product Distribution

| Feed | Temp. | Feed Rate mM/g cat/hr | % Yield Neopentanol | Neopentane | i-Butane | i-Pentane |
|---|---|---|---|---|---|---|
| Pivalic acid/hexane (80.6:19.4 wt.) | 325° C. | 0.8 | 0 | 68 | 28 | 4 |
| | | 1.6 | 61 | 25 | 14 | 0 |
| | | 3.2 | 76 | 14 | 10 | 0 |
| | | 6.4 | 84 | 8 | 8 | 0 |
| Pivalic acid/methanol (83.2:16.8 wt.) | 350° C. | 0.2 | 0 | 68 | 25 | 7 |
| | | 0.4 | 0 | 70 | 26 | 4 |
| | | 0.8 | 0 | 61 | 36 | 3 |
| | | 1.6 | 0 | 55 | 42 | 2 |
| | | 3.25 | 42 | 28 | 29 | 1 |
| | | 4.9 | 61 | 17 | 21 | 1 |

Complete conversion of pivalic acid occurred at 35.2–70.3 Kg/cm$^2$. Neopentane yields increased with increasing pressure. At the lowest pressure used, some neopentanol was produced. Therefore, conversion of neopentanol to neopentane is at least partially dependent on partial pressure of hydrogen. It is expected that higher selectivity toward neopentane could be obtained at pressures above 70.3 Kg/cm$^2$.

Selectivity toward isobutane production decreased with increasing pressure; selectivity toward isopentane was not substantially affected.

EXAMPLE 15

The effect of substrate feed rate on conversion and product distribution was studied using pivalic acid, admixed with methanol or with hexane. The experiments were done at 325° C. and 350° C., at a pressure of 70.3 Kg/cm$^2$, and hydrogen GHSV of 4500. The catalyst was 2:1 CuO/ZnO/10% alumina. Results are shown in Table 3.

At both of the temperatures studied, pivalic acid substrate was completely converted to products. Neopentane yields increased with decreasing substrate feed rates; the optimum was about 0.2–2.2 mM/g catalyst/h at both 325° C. and 350° C. Decreasing substrate feed rates gave corresponding lower increases in isobutane and neopentane yields. Neopentanol yields also increased with increasing substrate feed rates.

EXAMPLE 16

The effect of variations in catalyst composition was studied, using 2:1 or 3:1 CuO/ZnO/10% alumina catalysts.

Reduction of pivalic acid was carried out at 70.3 Kg/cm$^2$ and 4500 GHSV for hydrogen, using pivalic acid, admixed with methanol or hexane, at a substrate feed rate of 1.6 mM/g catalyst/h. Results of these experiments are shown in Table 4. It is apparent that, although the behavior of the catalysts is not identical, each of the catalysts gave neopentane as the major product (about 50% yield) at 350° C. and each of the catalysts gave neopentanol as the major product at 325° C. It is therefore expected that a variety of CuO/ZnO/alumina catalysts can be used for carrying out the synthesis of this invention.

EXAMPLE 17

The effect of diluent, admixed with pivalic acid, was determined, using hexane and methanol as typical cases. The experiments were done using 2:1 CuO/ZnO/10% alumina catalyst at 70.3 Kg/cm$^2$, at 4500–6000 GHSV for hydrogen and pivalic acid substrate feed rate of 1.6 mM/g catalyst/h. Results obtained were:
A. Pivalic acid/hexane (20% by weight), 50 h on line
   47 mol % neopentane
   49 isobutane
   4 isopentane B. Pivalic acid/methanol (15% by weight), 79 h on line 48 mol % neopentane
50 isobutane
2 isopentane The results, using two different diluents, accordingly vary only within limits of experimental error and show that product distribution is essentially unaffected by diluent. These results indicate that solvents of widely varying polarity give essentially identical results and that a wide variety of solvents can be employed in the practice of this invention.

TABLE 4

Comparison of Hydrogenation Catalysts

| Feed | Reaction Temperature | Catalyst[a] | % Yield Neopentanol | Neopentane | i-Butane | i-Pentane |
|------|------|------|------|------|------|------|
| A | 325° C. | 2:1 | 61 | 25 | 14 | 0 |
| B |  | 3:1 | 48 | 31 | 20 | 1 |
| B | 350° C. | 2:1 | 0 | 51 | 47 | 2 |
| B |  | 3:1 | 0 | 48 | 51 | 1 |

A Pivalic acid/hexane(80.6:19.4 wt.)
B Pivalic acid/methanol(85.7:14.3 wt.)
[a]Ratio indicates CuO/ZnO by weight, balance is alumina (10%)

EXAMPLE 18

The reproducibility of catalyst performance and catalyst life were studied in a series of experiments using 2:1 and 3:1 CuO/ZnO/10% alumina catalysts at 350° C., 70.3 Kg/cm² pressure, hydrogen GHSV of 4500–6000 and substrate feed rate of 1.6 mM/g catalyst/h.

The catalysts were activated at temperatures ranging from 250°–375° C. Reaction conditions, such as temperature, substrate feed rates, type of substrate feed, hydrogen flow rate and reaction pressures were changed throughout the experiments.

Results are shown in Table 5. It is apparent that variation in reaction conditions had little effect on catalyst performance, at least within the ranges investigated. It is further apparent that catalyst activity was unaffected after nearly 100 h on line.

EXAMPLE 19

The time required from the start of substrate feeding to reaching a steady-state product composition was determined at 350° C., using pivalic acid/methanol feed (85.7:14.3 by weight), 3:1 CuO/ZnO/10% alumina catalyst, pressure of 70.3 Kg/cm², 4500 GHSV for hydrogen and 1.6 mM/g catalyst/h feed rate for the substrate. Results are shown in Table 6. These results show that a steady state composition and mass balance above 95% was reached at the end of about 2 h on line in the reactor configuration and under the conditions used.

EXAMPLE 20

(a) An experiment is done, otherwise as in Example 3, using ethanol instead of methanol. Similar results are obtained.

(b) An experiment is done, otherwise as in Example 2, using octane as cosolvent. Similar results are obtained.

(c) An experiment is done, otherwise as in Example 1, using molten pivalic acid as the feed. Results are similar to those of Example 1.

(d) An experiment is run, otherwise as in Example 2, using as feed molten neopentanol. Results are comparable to those of Example 2.

TABLE 5

Reproducibility of Catalyst Performance at "Standard" Conditions

| Feed | Catalyst[a] | Hours On Line | Prior Conditions | % Yield neoC$_5$OH | neo-C$_5$ | i-C$_4$ | i-C$_5$ |
|------|------|------|------|------|------|------|------|
| A | 2:1 | 48 | 250–300° C. | 0 | 59 | 39 | 2 |
|   |   | 57 | 250 and 350° C. | 0 | 59 | 39 | 2 |
| B | 2:1 | 22 | 325–350° C. | 0 | 45 | 34 | 21 |
| C | 2:1 | 12 | 62 hr run using feed B | 0 | 47 | 48 | 5 |
|   |   | 24 | +350° C. | 0 | 47 | 47 | 6 |
|   |   | 30 | +325–375° C. | 0 | 46 | 49 | 5 |
|   |   | 50 | +feed rate switching | 0 | 47 | 49 | 4 |
| D | 2:1 | 14 | 375° C. | 0 | 51 | 47 | 2 |
|   |   | 73 | +H$_2$ flow switching | 0 | 51 | 47 | 2 |
|   |   | 79 | +H$_2$ flow switching | 0 | 48 | 50 | 2 |
|   |   | 98 | +pressure switching | 0 | 50 | 49 | 1 |
| E | 3:1 | 16 | 350° C. | 0 | 48 | 51 | 1 |
| F | 2:1 | 29 | 350° C. | 0 | 55 | 43 | 2 |

A Pivalic acid/methanol(50:50 wt.)
B Neopentanol/hexane(66.7:33.3 wt.)
C Pivalic acid/hexane(80.6:19.4 wt.)
D Pivalic acid/methanol(85.7:14.3 wt.)
E Pivalic acid/methanol(85.7:14.3 wt.)
F Pivalic acid/methanol(83.2:16.8 wt.)
[a]Ratio indicates CuO/ZnO by weight; balance is alumina (10%)

TABLE 6

Catalyst Lineout

| Hours On line | Product Yield, %* neoC$_5$ | i-C$_4$ | i-C$_5$ | Material Balance** | Normalized Product Yield*** neoC$_5$ | i-C$_4$ | i-C$_5$ |
|------|------|------|------|------|------|------|------|
| 0.3 | 14.8 | 4.2 | 1.0 | 20.0 | 74.0 | 21.0 | 5.0 |
| 1.0 | 46.2 | 41.8 | 1.6 | 89.6 | 51.6 | 46.7 | 1.8 |
| 1.5 | 45.9 | 46.0 | 1.6 | 93.5 | 49.1 | 49.2 | 1.7 |
| 2.0 | 46.5 | 47.9 | 1.8 | 96.2 | 48.3 | 49.8 | 1.9 |
| 2.5 | 47.0 | 69.1 | 1.6 | 97.7 | 48.1 | 50.3 | 1.6 |
| 3.0 | 47.7 | 50.4 | 1.6 | 99.7 | 47.8 | 50.6 | 1.6 |
| 4.0 | 46.2 | 48.9 | 1.6 | 96.6 | 47.8 | 50.6 | 1.6 |
| 5.0 | 46.0 | 49.5 | 1.6 | 97.0 | 47.4 | 51.0 | 1.6 |
| 7.0 | 45.4 | 48.3 | 1.6 | 95.2 | 47.7 | 50.7 | 1.6 |
| 10.0 | 48.0 | 52.7 | 1.6 | 102.2 | 47.0 | 51.6 | 1.5 |
| 13.0 | 46.9 | 50.6 | 1.6 | 99.0 | 47.4 | 51.1 | 1.5 |
| 16.0 | 45.7 | 49.1 | 1.3 | 96.1 | 47.6 | 51.1 | 1.4 |

*(FID area product/FID area feed) × 100
**sum of product yield
***(product yield/material balance) × 100

EXAMPLE 21

An experiment is done, otherwise as in Example 5, in which the hydrogen flow rate is 553 ml/min. Results ae similar to those of Example 5.

EXAMPLE 22

(a) Nickel on alumina (33% by weight of nickel) was prepared by impregnating gamma-alumina with an aqeuous solution of nickel nitrate. The catalyst was extruded, calcined and reduced at 350° C. for 16 h under a stream of 2% hydrogen in nitrogen.

(b) The nickel/alumina catalyst (33% Ni) thus prepared (4.00 g) was used for hydrogenation of neopentanol (49% by weight in n-hexane) at 260° C., under a pressure of 14 Kg/cm$^2$, 1500 GHSV for hydrogen and substrate feed rate of 1.1 mM/g catalyst/h. The products were 27 mol % of neopentane, 69% of methane and traces of other hydrocarbons. Neopentanol conversion was complete.

This experiment shows that other types of hydrogenation catalysts can be used for producing neopentane from neopentanol, but that significant carbon chain cleavage may occur.

EXAMPLE 23

The nickel/alumina catalyst (4.00 g) of Example 22 was used for hydrogenation of pivalic acid (55% by weight in n-hexane) at 200° C., a pressure of 35 Kg/cm$^2$, hydrogen GHSV of 1500 and substrate feed rate of 1.1 mM/g catalyst/h. The products under steady state operation were 24 mol % of neopentanol, 11 mol % of neopentane, 3 mol % of isopentane, 40 mol % isobutane and traces of other hydrocarbons and unconverted pivalic acid.

This example shows that lower reaction temperatures result in incomplete conversion to hydrocarbons and that, with the temperature and catalyst used, substantial demethylation occurs.

EXAMPLE 24

(a) Large-pore zeolite was impregnated with a solution of copper and zinc salts. The catalyst was reduced, prior to use, at 350° C. for 16 h under a stream of 2% hydrogen in nitrogen.

(b) Copper oxide/zinc oxide on zeolite (4.00 g) was used for hydrogenation of neopentanol (49 weight % in n-hexane) at 300° C., pressure of 70 Kg/cm$^2$, hydrogen flow rate of 4680 GHSV and substrate feed rate of 1.1 mM/g catalyst/h. The product contained 1% of neopentane. The balance of the product was isomerized hydrocarbons. Neopentanol conversion was complete.

This experiment shows that variation in catalyst support, low temperature and high hydrogen flow rate change the product mix.

EXAMPLE 25

Nickel/alumina catalyst of Example b 22 (4.00 g) was used for hydrogenation of pivalic acid (55 weight % in n-hexane) at 175° C., a pressure of 14 Kg/cm$^2$, hydrogen flow rate of 1500 GHSV and substrate feed rate of 1.1 mM/g catalyst/h. The product contained 81 mol % of neopentanol, 13 mol % of unconverted pivalic acid and traces of other hydrocarbons.

This experiment shows that temperatures below 250° C., particularly in the presence of a nickel catalyst, favor formation of intermediate neopentanol, rather than complete hydrogenation to neopentane.

EXAMPLE 26

(a) Neodecanoic acid ($R_1$ and $R_2$ are methyl, $R_3$ is alkyl of six carbon atoms) in hexane (50% by weight) was fed to a reactor charged with 4.00 g of 2:1 CuO/ZnO/10% alumina catalyst. The feed rate was 6 ml/h, the hydrogen flow rate 300 ml/min at STP, the pressure 70.3 Kg/cm$^2$ and the temperature 375° C.

The product under steady state conditions contained 29 mol % of neodecane, 6 mol % of neodecanol and 52 mol % of isononanes. The conversion of acid was 88 mol %, and the selectivity towards neodecane product 33%.

(b) Under conditions, otherwise as in part (a), but at a temperature of 350° C. and pressure of 17.6 Kg/cm$^2$, the product under steady state conditions contained 0.3 mol % of neodecane, 5.2 mol % of neodecanol and 2.7 mol % of isononanes. Based on 8% conversion of the acid, selectivity toward the neodecanol product was 64%.

We claim:

1. In a process for the synthesis of an alkyl-substituted 1,1,1-trialkylalkane of the formula $R_1R_2R_3CCH_3$ by hydrogenation, wherein $R_1$, $R_2$ and $R_3$ are the same or different alkyl of 1–10 carbon atoms in the presence of a hydrogenation catalyst and hydrogen, the improvement which comprises hydrogenating a feed of a neoacid of the formula $R_1R_2R_3CCOOH$, at a temperature from about 325° C. to about 375° C.; a hydrogen feed rate of 1500 to 8000 ml/g catalyst/h; a neoacid feed rate of 0.2 to 4.9 mM/g catalyst/h and a hydrogen pressure of 35–140 Kg/cm$^2$ over a copper oxide/zinc oxide catalyst comprising 80–95% by wt. of copper oxide/zinc oxide in an 8:1 to 1:1 weight ratio and 20–5% by weight alumina to obtain substantially complete conversion of the neoacid and recovering a product containing at least about 15 mol % yield of neoalkane based on the neoacid feed.

2. The process of claim 1, wherein $R_1$ and $R_2$ are methyl.

3. The process of claim 1, wherein $R_1$, $R_2$ and $R_3$ are methyl.

4. The process of claim 1, wherein $R_1$ and $R_2$ are methyl and $R_3$ is alkyl of six carbon atoms.

5. The process of claim 1, wherein $R_1$, $R_2$ and $R_3$ are methyl; the temperature is 335°–365° C.; the hydrogen feed rate is 4000–6000 ml/g catalyst/h; the neoacid substrate feed rate is 0.2–2.2 mM/g catalyst/h and the pressure is 56–70 Kg/cm$^2$.

6. The process of claim 1, wherein the neoacid feed is undiluted.

7. The process of claim 1, wherein the neoacid feed is diluted with 5–50% by weight of methanol.

8. The process of claim 1, wherein the neoacid feed is diluted with 5–50% by weight of hexane.

9. The process of claim 1, including a further step of purifying product containing neoalkanes by adsorbing by-products, produced by isomerization or demethylation and containing secondary carbon atoms, on a medium pore zeolite or molecular sieve.

10. The process of claim 9, wherein $R_1$, $R_2$ and $R_3$ are methyl and the by-product adsorbed by the zeolite or molecular sieve is isopentane or isobutane, or a mixture thereof.

11. The process of claim 1, including the further step of purifying the product by distillation.

12. The process of claim 1, wherein the catalyst is activated by treatment with 1–10% by volume of hydrogen in nitrogen at 250°–375° C. for 2–30 h.

13. In a process for the synthesis of an alkyl-substituted 1,1,1-trialkylalkane of the formula $R_1R_2R_3CCH_3$ by hydrogenation, wherein $R_1$, $R_2$ and $R_3$ are the same or different alkyl of 1–10 carbon atoms in the presence of a hydrogenation catalyst and hydrogen, the improvement which comprises hydrogenating a feed of a neoalcohol of the formula $R_1R_2R_3CCH_2OH$, at a temperature from about 325° C. to about 375° C.; a hydrogen feed rate of 1500 to 8000 ml/g catalyst/h; a neoalcohol feed rate of 0.2 to 4.9 mM/g catalyst/h and a hydrogen pressure of 35–140 Kg/cm$^2$ over a copper oxide/zinc oxide catalyst comprising 80–95% by wt. of copper oxide/zinc oxide in an 8:1 to 1:1 weight ratio and 20–5% by weight alumina to obtain at least about 40% conversion of the neoalcohol and recovering a product containing at least about 15 mol % yield of neoalkane based on the neoalcohol feed.

14. The process of claim 13, wherein the catalyst comprises 80–95% by weight of copper oxide/zinc oxide in 4:1 to 1:1 weight ratio and 20–5% by weight of alumina.

15. The process of claim 13, wherein $R_1$ and $R_2$ are methyl.

16. The process of claim 13, wherein $R_1$, $R_2$ and $R_3$ are methyl.

17. The process of claim 13, wherein the temperature is 335°–365° C., the pressure is 56–70 Kg/cm$^2$, the hydrogen flow rate is 4000–6000 ml/g catalyst/h and the neoalcohol feed rate is 0.2–2.2 mM/g catalyst/h.

18. The process of claim 13, wherein the neoalcohol is diluted with 5–50% by weight of methanol.

19. The process of claim 13, wherein the neoalcohol is diluted with 5–50% by weight of hexane.

20. The process of claim 13, wherein the neoalcohol is undiluted.

21. The process of claim 13, including the further step of purifying the product by distillation.

22. The process of claim 13, including a further step of purifying product containing neoalkanes by adsorbing by-products, produced by isomerization or demethylation and containing secondary carbon atoms, on a medium pore zeolite or molecular sieve.

23. The process of claim 22, wherein $R_1$, $R_2$ and $R_3$ are methyl and the by-product adsorbed by the zeolite or molecular sieve is isopentane or isobutane, or a mixture thereof.

24. The process of claim 13, wherein the catalyst is activated by treatment with 1–10% by volume of hydrogen in nitrogen at 250°–375° C. for 2–30 h.

25. The process of claim 1 wherein the product comprises a mixture of at least a neoalkane and a neoalcohol and the neoalcohol is separated from the product and is used as the feed to the process of claim 17.

26. The process of claim 25, wherein $R_1$ and $R_2$ are methyl.

27. The process of claim 25, wherein $R_1$, $R_2$ and $R_3$ are methyl.

28. The process of claim 25, wherein the temperature is 225°–300° C. and the hydrogen pressure is 35–70 Kg/cm$^2$.

* * * * *